(12) United States Patent
Kuehl et al.

(10) Patent No.: US 9,217,658 B2
(45) Date of Patent: Dec. 22, 2015

(54) VAPORIZER ANESTHESIA LEVEL DETECTOR

(75) Inventors: Kenneth J. Kuehl, Oregon, WI (US); Michael Jones, Sun Prairie, WI (US); William Breckenridge McHenry, Fort Atkinson, WI (US); Shawn Thomas Whitman, Cambridge, WI (US)

(73) Assignee: General Electric Company, Schenectady, NY (US)

( * ) Notice: Subject to any disclaimer, the term of this patent is extended or adjusted under 35 U.S.C. 154(b) by 554 days.

(21) Appl. No.: 13/436,265

(22) Filed: Mar. 30, 2012

(65) Prior Publication Data

US 2013/0255676 A1  Oct. 3, 2013

(51) Int. Cl.
*G01F 23/26* (2006.01)
*G01F 23/02* (2006.01)

(52) U.S. Cl.
CPC .............. *G01F 23/265* (2013.01); *G01F 23/02* (2013.01); *G01F 23/266* (2013.01); *G01F 23/268* (2013.01)

(58) Field of Classification Search
CPC ..... G01F 23/02; G01F 23/007; G01F 23/265; G01F 23/242; G01F 23/26; G01F 23/261; G01F 23/263; G01F 23/268; G01F 23/266; Y10S 261/65

USPC ............. 73/323, 304 C, 290 R, 325; 324/691
See application file for complete search history.

(56) References Cited

U.S. PATENT DOCUMENTS

| | | | | |
|---|---|---|---|---|
| 5,133,212 A | * | 7/1992 | Grills et al. | 73/296 |
| 6,164,132 A | * | 12/2000 | Matulek | 73/304 C |
| 6,529,845 B1 | * | 3/2003 | Beck, II | 702/100 |
| 7,432,725 B2 | | 10/2008 | Sieh et al. | |
| 7,889,345 B2 | | 2/2011 | Shang et al. | |
| 2004/0147038 A1 | * | 7/2004 | Lewis et al. | 436/149 |
| 2005/0229974 A1 | * | 10/2005 | Tschanz | 137/386 |
| 2007/0216424 A1 | * | 9/2007 | Sieh et al. | 324/662 |
| 2008/0087283 A1 | * | 4/2008 | Cromack et al. | 128/203.12 |
| 2010/0294035 A1 | * | 11/2010 | Naydenov | 73/304 C |
| 2011/0056490 A1 | * | 3/2011 | Kullik et al. | 128/203.12 |

* cited by examiner

*Primary Examiner* — Hezron E Williams
*Assistant Examiner* — Marrit Eyassu

(57) ABSTRACT

A vaporizer including a reservoir for storing an anesthetic liquid agent and a vaporizing element configured to vaporize the anesthetic liquid agent. A level detector is located outside of and adjacent to the exterior of the reservoir. The level detector includes at least one electrical field sensor configured to provide an output voltage signal based upon the capacitance of material within the reservoir proximate the electrical field sensor. The vaporizer includes a display providing a visual indication of the amount of liquid anesthetic agent in the reservoir.

6 Claims, 3 Drawing Sheets

VAPORIZER ANESTHESIA LEVEL DETECTOR

BACKGROUND OF THE INVENTION

The present invention relates generally to measuring the level of anesthetic agents in an anesthesia vaporizer.

An anesthesiologist monitors the level of anesthetic agent in the vaporizer to ensure sufficient anesthetic agent is available for treatment of a patient. The level of the anesthetic agent may be viewed through a glass tube or transparent portion of the vaporizer referred to as a sight glass. As the anesthetic agent is vaporized, the liquid level of the anesthetic agent can be seen visually to fall in the sight glass of a glass providing a visual indication as to the level of anesthetic agent remaining in the vaporizer.

BRIEF DESCRIPTION OF THE INVENTION

One embodiment includes a vaporizer including a reservoir for storing an anesthetic liquid agent and a vaporizing element configured to vaporize the anesthetic liquid agent. A level detector is located outside of and adjacent to the exterior of the reservoir. The level detector includes at least one electrical field sensor configured to provide an output voltage signal based upon the capacitance of material within the reservoir proximate the electrical field sensor. The vaporizer includes a display providing a visual indication of the amount of liquid anesthetic agent in the reservoir.

In another embodiment a level detector is used with an existing liquid anesthesia vaporizer having a sight glass operatively connected to a reservoir configured to hold a liquid anesthetic agent. The level detector includes a housing supporting at least one electrical field sensor configured to provide an output voltage signal based upon the capacitance of material proximate the electrical field sensor. The housing is positioned proximate the vaporizer such that the electrical field sensor is adjacent the sight glass, the electrical field sensor is configured to provide an output voltage signal that changes as the capacitance of material within the sight glass changes.

In another embodiment, a method of detecting the level of liquid anesthetic agent within a vaporizer includes providing a level detector outside of and adjacent to a reservoir of the vaporizer. The level detector includes a plurality of electrical field sensors providing an output voltage signal based upon the capacitance of material within the reservoir proximate the electrical field sensor. The output voltage of each electrical field sensor as the liquid anesthetic agent is being vaporized is received at the processing unit. The percent of the liquid anesthetic agent remaining in the reservoir is displayed on a display as a function of the sampled output voltage values of the electrical field sensors.

DETAILED DESCRIPTION

Figure 1:
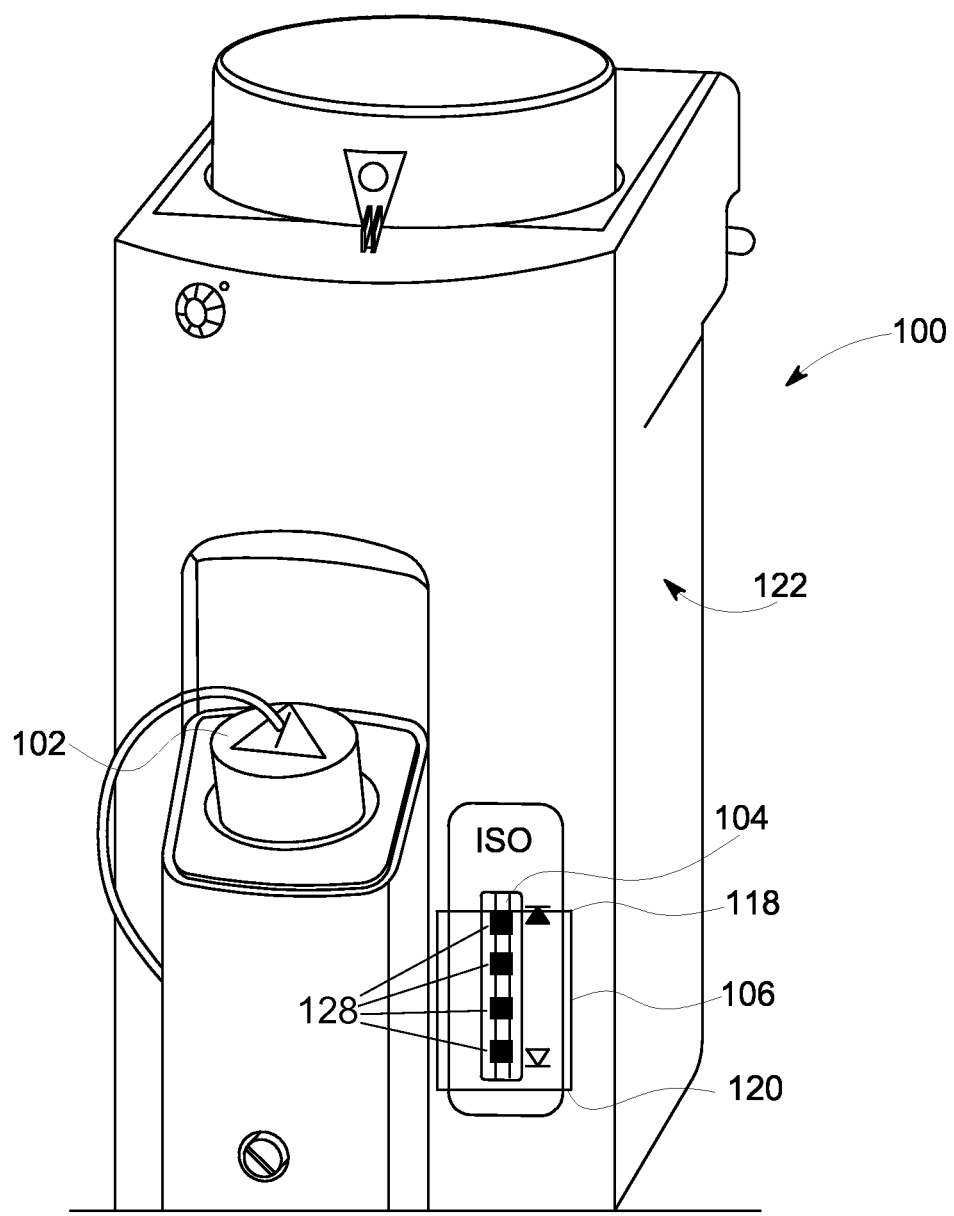
FIG. 1 is a vaporizer with an anesthesia level detector.

Referring to FIG. 1, a vaporizer 100 removably receives an anesthetic container 102 containing an anesthetic agent. Vaporizer 100 includes an internal reservoir holding the liquid anesthetic agent prior to be being vaporized. A sight glass 104 provides an indication of the level of liquid anesthetic agent remaining in the reservoir and/or anesthetic container. A level detector 106 detects the level of liquid anesthetic within the sight glass and/or reservoir.

Figure 2:
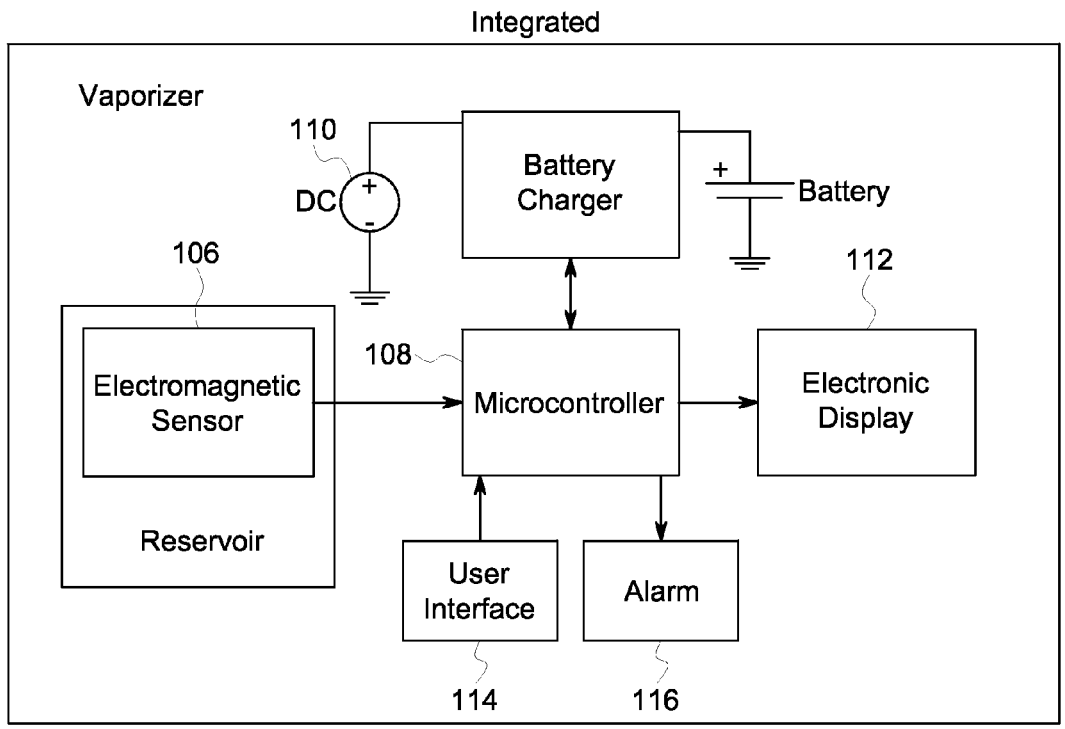
FIG. 2 is a schematic illustration of an anesthesia level detector integrated with a vaporizer.

Referring to FIG. 2 a schematic view of vaporizer 100 includes a level detector 106 adjacent to sight glass 104 and operatively coupled to a microcontroller or processing unit 108. An electrical source 110 provides power for level detector 106, the processing unit 108 and a display 112. However, it is also contemplated that the processing unit and/or the display 112 would have an electrical source separate from one another and the level detector 106. A user interface 114 is operatively connected to processing unit 108 and an alarm 116 provides an audible sound upon a receiving a signal from processing unit 108 that a certain preset condition has been reached. In another embodiment, alarm 116 may provide a visual light source such as a colored light, flashing light, or some other light source to indicate a present condition has been reached.

The term "processing unit" shall mean a presently developed or future developed processing unit that executes sequences of instructions contained in a memory. In one example the term "memory" as used herein comprises a non-transient computer-readable medium containing computer code for the direction of controller. Execution of the sequences of instructions causes the processing unit comprising controller to perform steps such as providing power to level detector, processing signals received from the level detector, and providing signals to the display. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, processing unit 108 may be embodied as part of one or more application-specific integrated circuits (ASICs). Unless otherwise specifically noted, the processing unit is not limited to any specific combination of hardware circuitry and software, nor to any particular source for the instructions to be executed.

In one embodiment sight glass 104 is a glass member having a generally vertical axis in the direction of gravity allowing visual access into the anesthetic reservoir within vaporizer 100. While the sight glass may have other axis, such as at an angle other than 90 degrees to the earth's surface, the level of the liquid shown from a lowest point to a highest point provides an indication of the amount of anesthetic agent within the vaporizer. In another embodiment, sight glass 104 is separate from but in fluid communication with the vaporizer reservoir providing an indication of the height level of the anesthetic agent within the reservoir and/or container 102.

When the reservoir is full, the level of liquid as viewed through the sight glass by an operator or anesthesiologist will be proximate an upper edge sight glass 118. As the liquid anesthetic is vaporized the level of the liquid vaporizer drops to proximate lower edge 120 of sight glass 104. Detector 106 is positioned adjacent to sight glass 104 on the outside of the sight glass away from the interior of the reservoir such that detector 106 is not in contact with the liquid anesthetic. Detector 106 may be located on a portion of the reservoir that is not visible outside of a housing wall 122 of vaporizer 100, but rather may be located between the reservoir and housing 122. In one embodiment detector 106 is in contact with sight glass 104 and visible from the outside of housing 122 and alternatively in another embodiment, detector 106 may be adjacent to outside wall of the reservoir and not adjacent to sight glass 104 that is visible to an operator. The outside wall of the reservoir may or may not be transparent. In one embodiment, detector 106 may be adjacent a portion of the outside wall of the reservoir that is not transparent and may be opaque.

Detector 106 in one embodiment includes an electromagnetic field sensing element configured to detect a change in capacitance (referred to herein as an E-field sensor or electrical field sensor). The output of an E-field sensor is responsive to the dielectric constant of objects within its electrical field. Detector 106 includes a number of the E-field sensors 128 spaced along the vertical (up/down) axis of sight glass 104 or proximate an outer wall of the reservoir. The sight glass 104, the E-field sensor constructed such to be fully enclosed within the sump, or outer wall of the reservoir supporting the E-field sensors are formed from a glass, polyimide or other non-metallic materials in which the presence of the liquid anesthetic within the electrical field of the E-field sensors can be detected. The glass, polyimide or other non-metallic materials may be opaque. E-field sensors can detect a change in the dielectric constant of materials on an opposite side of non-metallic materials. This feature allows an E-field sensor to detect a change in the level of the liquid anesthetic agent in a non-metallic reservoir or sight glass without having to be in actual contact with the liquid anesthetic agent.

The capacitance of an E-field sensor changes as the dielectric constant of the material within the electromagnetic field of the particular E-field sensor changes. The change in capacitance is measured as a change in voltage of an E-field sensor. Different materials have different dielectric constants and the same material in different phases have different dielectric constants. The different dielectric constants have a different impact on the capacitance of the E-field sensor and as a result an impact on the output voltage of an E-Field sensor. For example, the dielectric constant for air is 1.0 while the dielectric constant for water is 78.5. It is believed that some liquid anesthetic agents have a dielectric constant between 4.0 and 6.0. When air is within the electrical field of the E-field sensor the capacitance of the E-field sensor will produce a given output voltage. When a liquid such as water or an anesthetic agent is within the electrical field of the E-field sensor, the capacitance of the E-field sensor will change providing a different output voltage than the output voltage of the E-field sensor that is adjacent air.

When the anesthetic reservoir is full with liquid anesthetic agent having a dielectric constant between 4.0 and 4.5 the capacitance of an E-Field sensor will impact the output voltage of the E-Field sensor. As the liquid anesthetic agent in the reservoir is vaporized the level of liquid anesthetic agent in the reservoir will drop and a combination of air and anesthetic agent in a vapor phase will be present in the reservoir above the liquid anesthetic agent. This combination of air and vapor anesthetic agent will have a lower dielectric constant than the liquid anesthetic agent and as a result the capacitance of the E-field sensor will change and will measured as a change in the output voltage of the E-Field sensor. As described in more detail below, the change is voltage output provides an indication of the level of the liquid anesthetic remaining in the reservoir.

In one example detector 106 includes ten E-field sensors evenly spaced apart from one another between the lower lever 120 and upper lever 118 of sight glass 106, or corresponding positions adjacent the liquid anesthetic reservoir. In this manner ten sensor zones are created. The first zone is defined as the region between the bottom of the reservoir or lower level 120 of the sight glass 104 and the position of the first E-field sensor which is intermediate lower level 120 and upper level 118. Similarly, the second zone is located between the first E-field sensor and the upper level 118. In this manner additional sensors are positioned between each subsequent E-field sensor and the upper level. It is also contemplated that there may be less than ten sensors. In one embodiment there are between two and ten sensors and in another embodiment there may be more than ten sensors. In a further embodiment a single E-field sensor is used to provide an alarm or indication when an operator should be alerted to a low liquid anesthetic agent condition. The location of a single sensor could be at a location indicating that the level of liquid anesthetic in the reservoir is less than or equal to twenty five percent (25%) of the capacity of the reservoir. In another embodiment the location of the single E-field sensor may be at a position indicating that the level of liquid anesthetic is less than or equal to ten percent (10%) of the capacity of the reservoir.

In addition to E-field sensors used to detect a change in the capacitance caused by a change in the dielectric constant between the liquid anesthetic agent and the vapor anesthetic, an additional control E-field sensor may be used that is exposed to a region of the reservoir or sight glass that does not have any liquid anesthetic agent during operation of the vaporizer. This additional control E-field sensor may provide a base line for comparison with the other E-field sensors.

When the reservoir is full, the processing unit 108 will obtain a start voltage output signal from each of the E-field sensors in detector 106. The start voltage output value may be stored in memory in the processing unit 108. As the vaporizer begins to vaporize the liquid anesthetic agent, the level of liquid anesthetic in agent the reservoir will fall. Once the level of liquid anesthetic agent drops below the region of the upper most E-Field sensor the output voltage of the upper most E-Field sensor will change since the dielectric constant of the air and/or anesthetic vapor is lower than the dielectric constant of liquid anesthetic agent.

When the vaporizer is in use, processing unit 108 receives the output voltage from each of the E-field sensors at regular predetermined intervals. Alternatively, each E-field sensor sends a signal to processing unit 108 only when a certain output voltage is obtained. The output voltage of each E-field sensor is compared to the corresponding start voltage output stored in memory. When the difference between the start value and updated voltage value is greater than a predetermined value the processor provides a signal to the display indicating the level of liquid vaporizer remaining in the reservoir. The predetermined value of the difference may be set to ensure that the change being detected represents a change of the level of anesthetic agent and not minor fluctuations caused by the system or minor changes within the anesthetic agent itself. A change in the makeup of the anesthetic agent due to impurities or contamination may cause a difference in the E-filed reading that may be of interest to an anesthesiologist but may not indicate a change of state from the liquid to a vapor. In one embodiment, such minor changes may trigger a warning signal that is distinct from a change in the level of anesthetic agent in the reservoir. Calibration of an E-Field sensor to a known dielectric constant may allow a noted change in the E-Field output to detect whether there are impurities or contaminates in the anesthetic agent. Additionally, if the E-Field sensor voltage output is different that a pre-set range of output of an E-Field sensor for a given anesthetic agent, it may indicate that the incorrect anesthetic agent is present.

As the output voltage in each successive E-field sensor drops below the predetermined value the level of liquid vaporizer as shown on the display may be reduced by a percent equal to the number of E-Field sensors meeting the criteria divided by the total number of E-Field sensors. In the example in which there are ten E-Field sensors and the two uppermost E-Field sensors are indicating a change in output voltage greater than a predetermined value, the display would show that there is a twenty percent (20%) reduction in the liquid anesthetic available in the reservoir or alternatively provide a some sort of visual indication that the reservoir is eighty percent (80%) full. The visual indication may be in the form of an electronic display that will be discussed further below.

In another embodiment, each E-field sensor output voltage is compared to the average output voltage of all of the E-field sensors. The number of E-field sensors with a voltage output lower than the average voltage value of all of the E-field sensor reading represents the number of E-field sensors that are proximate to air. If there are 10 evenly spaced E-field sensors along a vertical axis perpendicular to the direction of gravity, and 4 E-field sensors have readings below the average value of all of the E-field sensors, then it can be understood that 4 of 10 or 40% of the E-field sensors are no longer adjacent liquid vaporizer. Therefore the reservoir is 60% full of liquid anesthetic agent. Since the E-field sensor output voltage measurements proximate air will have a lower output voltage than the E-field senor readings proximate the liquid anesthetic, it can be determined that the E-field sensors that are lower than the average E-filed sensors at a given time represent the number of sensors no longer proximate the liquid anesthetic.

In an alternative method, the voltage output of each E-field sensor is aggregated when the reservoir is empty (the "Empty Voltage Value") and when the reservoir is full (the "Full Voltage Value"). By way of clarification, the Full Voltage Value is the sum of all of the E-Field voltage output when the reservoir is full of a liquid anesthetic liquid agent. While, the Empty Voltage Value is the sum of all of the E-Field voltage output when the reservoir is empty of any liquid anesthetic liquid agent, and is full of air. The difference between the Full Voltage Value (FVV) and the Empty Voltage Value (EVV) is referred to herein as the Differential Voltage Value (DVV). The Empty Voltage Value (EVV), the Full Voltage Value (FVV), and the Differential Voltage Value (DVV) are stored in memory by processing unit 108. The processing unit is configured to calculate the DVV and store the value in memory. As the vaporizer vaporizes the anesthetic liquid agent in the reservoir the voltage output of each E-field sensor is obtained at select point in the operation of the vaporizer. The voltage outputs of each E-filed sensor obtained during a specific sampling is aggregated and referred to herein as the Sample Voltage Value (SVV). The percent of liquid vaporizer remaining in the reservoir is calculated by processor 108 as the difference between the Sample Voltage Value and the Empty Voltage Value divided by the Differential Voltage Value which is mathematically represented as (SVV−EVV)/DVV. As the liquid level hovers about an E-field sensor the actual voltage value will decline not in a discrete manner but in a continuous manner as the liquid falls below the E-field sensor. The aggregate method discussed in this paragraph accommodates the varying change of the voltage output of adjacent E-field sensors as the liquid level approaches and falls below the E-field sensor. In one embodiment, each E-field sensor may be adjusted to provide a reading of zero (0.0) when the vaporizer reservoir is empty. In this case, the mathematical representation of the percent of remaining anesthetic agent would be SVV/FVV.

Figure 4:
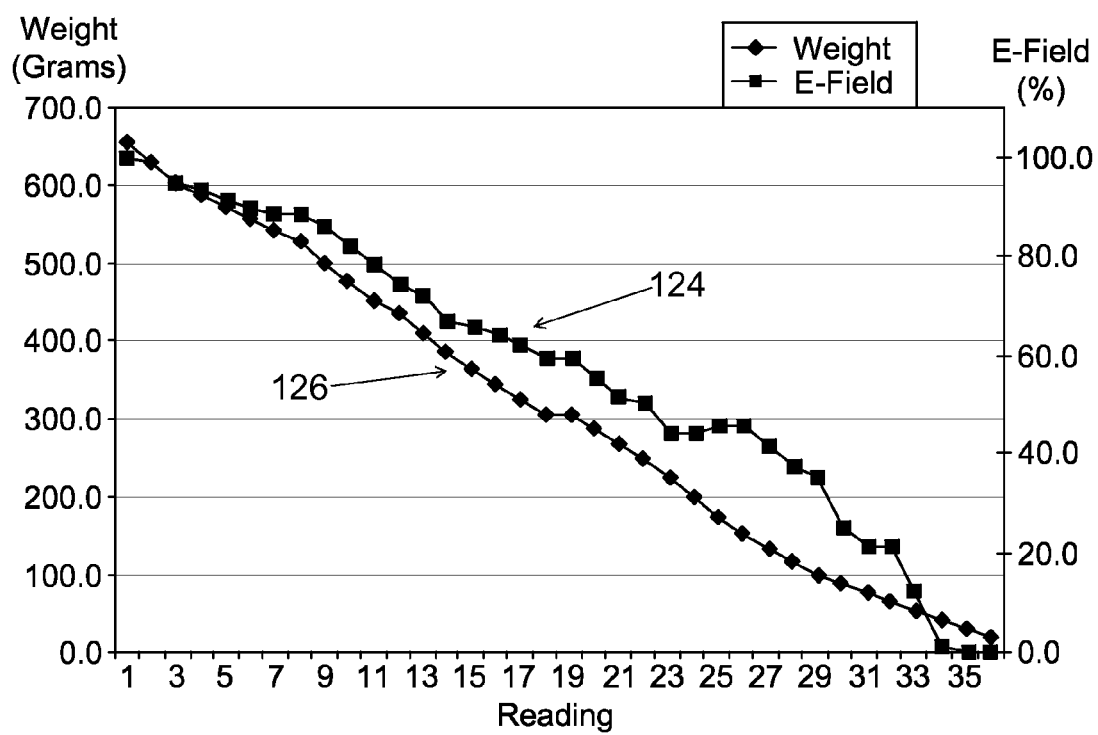
FIG. 4 is a graph illustrating the correlation between weight of a liquid anesthetic agent in a reservoir and the aggregate output of electrical field sensors.

In one test the weight of the anesthetic agent available in a test tube was compared to the aggregate differential voltage value as the anesthetic agent was vaporized. The weight is directly proportional to the volume in the test tube. Referring to FIG. 4 the x-axis represents the time over which measurements of weight and six E-Field sensors evenly spaced on a test tube representing a reservoir in an anesthesia vaporizer were obtained. The left y-axis indicates the weight in grams of the anesthetic agent remaining and the right y-axis indicates the aggregate E-Field readings of all of the E-field sensors. An E-field reading was taken at periodic intervals of time during which the anesthetic agent was vaporized as illustrated in FIG. 4. The output voltage of all of the E-field sensors were aggregated at each interval of time. The weight of the liquid anesthetic was measured at each interval of time that the output voltage of the E-field sensors were measured. The weight and aggregate sum of the E-field sensor voltage output was plotted for each unit of time. As illustrated in FIG. 4, the aggregate E-field readings 124 have a similar slope as the weight 126. Accordingly, the aggregate E-field readings provide a measure that can be correlated to the weight and therefor volume of anesthetic agent remaining in a liquid state in an anesthesia vaporizer reservoir. In this example and test, each E-field sensor was calibrated to have an output value of zero (0) when the test tube was empty of any anesthetic liquid agent.

Impurities or contaminates in an anesthetic agent will alter the dielectric constant. Calibration of an E-Field sensor to a known dielectric constant may allow a noted change in the E-Field output to detect whether there are impurities or contaminates in the anesthetic agent. In one embodiment, the voltage output of the E-field sensor is known for a given anesthetic agent having a known dielectric constant. The known voltage output is stored in the processor and is compared to an actual voltage reading of the E-field sensor when the reservoir is full. If the actual voltage output of the E-field sensor deviates from a predetermined acceptable range from the known output voltage of the E-field sensor of the given anesthetic agent it may indicate a problem with the anesthetic agent in the reservoir. An alarm and/or display will indicate that an operator should investigate to determine whether the correct anesthetic agent is being used or whether the anesthetic agent may include contaminates that have altered the dielectric constant of the anesthetic agent.

The voltage output of an E-field sensor will change as the level of liquid anesthetic agent drops through the E-field sensor electronic field. In this way, it is possible to determine the location of the level of the liquid anesthetic agent between E-field sensors. In one embodiment the E-field sensors are spaced apart from one another and calibrated so that the electronic fields of adjacent E-field sensors do not overlap one another but are closely adjacent to one another. In this orientation the level of liquid anesthetic will impact the voltage output of at least one E-field sensor regardless of the level of the liquid anesthetic. Stated another way, it is possible to determine the location of the liquid anesthetic agent between E-field sensors, since any change in the level of the liquid anesthetic will result in a change in the output voltage of at least one E-field sensor. The electronic field of an E-field sensor can be arranged so that the entire vertical height of the reservoir is covered by the electronic field of at least one E-field sensor. The voltage output of the E-field sensor will continuously change as the level of liquid anesthetic agent drops through the E-field sensor field. This continuous change in voltage output provides information to permit the processor to calculate the location of the liquid level within the electronic field of the E-field sensor.

Display 112 may provide a graphical illustration of the level of the liquid anesthetic remaining in the vaporizer in the form of a vertical bar extending from an "empty" indicia and a "full" indicia. However, other methods of graphical illustration to show the percent or amount of anesthetic agent remaining in the reservoir of the vaporizer may be used as well. Display 112 may also provide a numerical percentage of the anesthetic agent available in the vaporizer. The display may also provide textual information including the type of anesthetic agent in the vaporizer. The type of anesthetic agent may be input through user interface 114. Alternatively, the type of anesthetic agent may be determined by a comparison of the voltage output of the E-field sensor and compared to known voltage output of E-field sensors resulting from given known dielectric constant of anesthetic agents.

Referring to FIG. 2, level detector 106 is integrally formed with the vaporizer. In this embodiment, the power source 110 that powers the vaporizer may also be used to provide power to the level detector 106.

Figure 3:
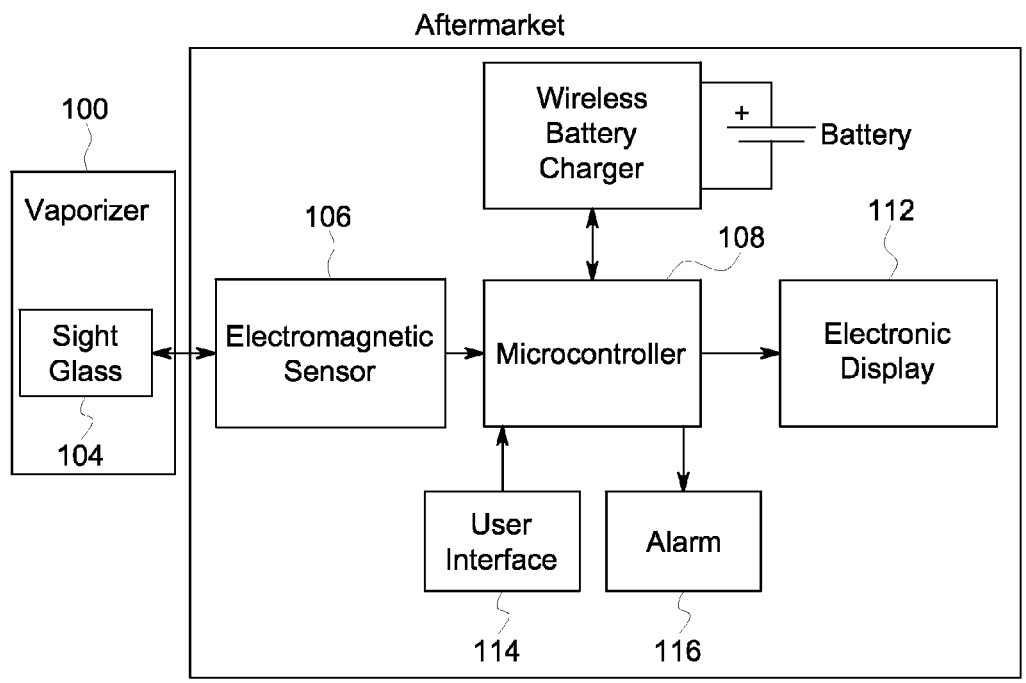
FIG. 3 is a schematic illustration of another embodiment of an anesthesia level detector separate from and operatively secured to a vaporizer.

Referring to FIG. 3, level detector 106 may be provided as a separate device and operatively secured to the sight glass 104 of a anesthesia vaporizer. In this embodiment, a housing supporting the level detector 106, processor 108, electrical source 110, display 112, user interface 114 and alarm 116 is placed adjacent to the site glass such that the E-field sensors of level detector 106 are closely adjacent sight glass 104 and/or reservoir. The housing may be secured to the vaporizer with mechanical fasteners to ensure proper alignment of the E-field sensors and the sight glass. This embodiment may be provided as an aftermarket device to provide information on the level and/or volume of anesthetic agent remaining in the vaporizer. This aftermarket level detector may include a battery providing sufficient electrical charge to power processor 108, display 112 and alarm 116 if required.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompasses a plurality of such particular elements.

What is claimed is:

1. A level detector for use with an existing liquid anesthesia vaporizer having a sight glass operatively connected to a reservoir configured to hold a liquid anesthetic agent including, the level detector comprising:
    a housing supporting at least one electrical field sensor configured to provide an output voltage signal based upon the capacitance of material proximate the electrical field sensor;
    a power source;
    a display;
    an input device; and
    a processing unit configured to obtain the voltage output of the electrical field sensor, wherein the processing unit is configured to obtain and store a first sum of the output voltage of all of the electrical field sensors when the reservoir is full of a liquid anesthetic agent and, periodically obtain a subsequent sum of the output voltage of all of the electrical field sensors and display the amount of liquid anesthetic agent remaining in the reservoir as a function of the ratio of the subsequent sum and the first sum
    the housing being positioned proximate the vaporizer such that the electrical field sensor is adjacent the sight glass, the electrical field sensor configured to provide an output voltage signal that changes as the capacitance of material within the sight glass changes.

2. The level detector of claim 1, wherein the at least on electrical field sensor includes at least four electrical field sensors arranged along a vertical axis.

3. The level detector of claim 1 wherein the at least one electrical field sensor is more than two electrical field sensors, each electrical field sensors being evenly spaced from an adjacent electrical field sensor and arranged along a vertical axis.

4. A level detector for use with an existing liquid anesthesia vaporizer having a sight glass operatively connected to a reservoir configured to hold a liquid anesthetic agent including, the level detector comprising:
    a housing supporting at least one electrical field sensor configured to provide an output voltage signal based upon the capacitance of material proximate the electrical field sensor;
    the housing being positioned proximate the vaporizer such that the electrical field sensor is adjacent the sight glass, the electrical field sensor configured to provide an output voltage signal that changes as the capacitance of material within the sight glass changes;
    wherein the housing includes a power source; a display; and an input device; and a processing unit;
    wherein the processing unit is configured to store in a memory a predetermined output value for each electrical field sensor, the processor receiving voltage output values from each electrical field sensor and providing instructions to the display to provide a visual indication of the percent of anesthetic remaining in the reservoir as a ratio of the number of electric field sensors below the predetermined value and the total number of electric field sensors.

5. A level detector for use with an existing liquid anesthesia vaporizer having a sight glass operatively connected to a reservoir configured to hold a liquid anesthetic agent including, the level detector comprising:
    a housing supporting at least one electrical field sensor configured to provide an output voltage signal based upon the capacitance of material proximate the electrical field sensor;
    the housing being positioned proximate the vaporizer such that the electrical field sensor is adjacent the sight glass, the electrical field sensor configured to provide an output voltage signal that changes as the capacitance of material within the sight glass changes;
    wherein the housing includes a power source; a display; and an input device; and a processing unit;
    wherein the processing unit is configured to receive an output voltage from each electrical field sensor and execute instructions from memory to calculate an average output voltage of all of the electrical field sensors, the processing unit executing instructions to determine the number of electrical field sensors below the average value output voltage and provide the ratio of electrical field sensors below the average value to the total number of electrical field sensors.

6. A level detector for use with an existing liquid anesthesia vaporizer having a sight glass operatively connected to a reservoir configured to hold a liquid anesthetic agent including, the level detector comprising:

a housing supporting at least one electrical field sensor configured to provide an output voltage signal based upon the capacitance of material proximate the electrical field sensor;

the housing being positioned proximate the vaporizer such that the electrical field sensor is adjacent the sight glass, the electrical field sensor configured to provide an output voltage signal that changes as the capacitance of material within the sight glass changes;

wherein the housing includes a power source; a display; and an input device; and a processing unit;

wherein the processing unit is configured to store an empty voltage value defined by the aggregate of the voltage output of each electrical field sensor when the reservoir is empty of an anesthetic liquid agent and full of air and store a full voltage value defined by the aggregate of the voltage output of each electrical field sensor when the reservoir is full of an anesthetic liquid agent, wherein the processing unit derives a differential voltage value as the difference between the full voltage value and the empty voltage value, the processing unit calculates a sample voltage value as the aggregate voltage output from all of the electrical field sensors at a time during use of the liquid anesthesia vaporizer and provides the percent of anesthetic remaining in the reservoir as the difference between the sample voltage value and the empty voltage value divided by the differential voltage value.

\* \* \* \* \*